United States Patent
Endo

(10) Patent No.: US 10,588,621 B2
(45) Date of Patent: Mar. 17, 2020

(54) MEDICAL NEEDLE

(71) Applicant: COSMIC M.E. INC., Kawaguchi-shi, Saitama (JP)

(72) Inventor: Masao Endo, Tokyo (JP)

(73) Assignee: COSMIC M.E.INC., Kawaguchi-Shi (JP)

( * ) Notice: Subject to any disclaimer, the term of this patent is extended or adjusted under 35 U.S.C. 154(b) by 0 days.

(21) Appl. No.: 15/321,308

(22) PCT Filed: Jul. 30, 2015

(86) PCT No.: PCT/JP2015/071652
§ 371 (c)(1),
(2) Date: Dec. 22, 2016

(87) PCT Pub. No.: WO2016/039035
PCT Pub. Date: Mar. 17, 2016

(65) Prior Publication Data
US 2017/0196552 A1    Jul. 13, 2017

(30) Foreign Application Priority Data
Sep. 11, 2014  (JP) .................................. 2014-184747

(51) Int. Cl.
*A61B 17/04* (2006.01)
*A61B 17/06* (2006.01)
*A61B 17/00* (2006.01)

(52) U.S. Cl.
CPC ...... *A61B 17/0485* (2013.01); *A61B 17/0469* (2013.01); *A61B 17/06004* (2013.01);
(Continued)

(58) Field of Classification Search
CPC .... A61B 2017/06052; A61B 17/32056; A61B 17/3417; A61B 10/0233;
(Continued)

(56) References Cited

U.S. PATENT DOCUMENTS 5,501,692 A * 3/1996 Riza .................. A61B 17/0469
112/169
9,924,938 B2 * 3/2018 Ziniti ................. A61B 17/0469
(Continued)

FOREIGN PATENT DOCUMENTS

| CN | 101721235 A | 6/2010 |
| EP | 1 908 408 A1 | 4/2008 |
| JP | 2007-252408 A | 10/2007 |

OTHER PUBLICATIONS

Iwade et al., "Laparoscopic Percutaneous Extraperitoneal Closure for Inguinal Hernia in Girls at Nagano Children's Hospital", The Shinshu Medical Journal, vol. 61, No. 3, 2013, pp. 139-147.
(Continued)

*Primary Examiner* — Erich G Herbermann
(74) *Attorney, Agent, or Firm* — Birch, Stewart, Kolasch & Birch, LLP

(57) ABSTRACT

The purpose of the present invention is to provide a medical needle with which, compared to a conventionally known suture thread guide needle, puncture, handling, and perforation are easy when guiding a suture thread along a hernia orifice beneath the skin, and therefore, the medical needle enables the execution of an LPEC method using simpler procedures. The purpose is accomplished by a medical needle comprising: a loop member provided with a loop needle the distal end of which has a loop-shaped structure, and a grip part the outer diameter of which is larger than the outer diameter of the loop needle; a threading member that is provided with a tubular threading needle and a tubular grip part the outer diameter of which is larger than the outer diameter of the threading needle, and that is configured so that the loop member can pass through the threading member from the distal end thereof; and a puncturing member that is provided with a tubular puncture needle the distal end of which has a sharp-angled structure and a tubular grip part
(Continued)

the outer diameter of which is larger than the outer diameter of the puncture needle, and that is configured so that the threading member can pass through the puncturing member from the distal end thereof.

5 Claims, 14 Drawing Sheets

(52) U.S. Cl.
CPC ........ *A61B 17/06066* (2013.01); *A61B 17/06* (2013.01); *A61B 17/06109* (2013.01); *A61B 2017/00818* (2013.01); *A61B 2017/00991* (2013.01); *A61B 2017/061* (2013.01); *A61B 2017/06019* (2013.01); *A61B 2017/06052* (2013.01)

(58) Field of Classification Search
CPC .. A61B 2017/00358; A61B 2017/2212; A61B 17/0485; A61B 17/221; A61B 17/12; A61B 17/12009; A61B 17/12013; A61B 2017/12004; A61L 17/00
See application file for complete search history.

(56) References Cited

U.S. PATENT DOCUMENTS

| | | |
|---|---|---|
| 2003/0045892 A1 | 3/2003 | Kaladelfos |
| 2006/0271074 A1* | 11/2006 | Ewers ............... A61B 17/0401 606/148 |
| 2007/0233188 A1* | 10/2007 | Hunt ............... A61B 17/00234 606/228 |
| 2008/0255591 A1* | 10/2008 | Harada ............. A61B 17/0469 606/148 |

OTHER PUBLICATIONS

Endo et al., "Laparoscopic completely extraperitoneal repair of inguinal hernia in children: a single-institute experience with 1,257 repairs compared with cut-down herniorrhaphy," Surgical Endoscopy, vol. 23, No. 8, DOI: 10.1007/s00464-008-0300-7, Apr. 3, 2009, pp. 1706-1712.

Endo et al., "Laparoscopic Hernia Repair and Its Validation by Second-Look Inspection to Internal Inguinal Rings in Children with Patent Processus Vaginalis," Laparoscopy—An Interdisciplinary Approach, ISBN: 978-953-307-299-9, Sep. 12, 2011, pp. 133-146.

European Patent Office Communication and extended search report issued in the corresponding European Patent Application No. 15840468.1 dated Mar. 6, 2018.

European Office Action dated Feb. 28, 2019, for European Application No. 15840468.1.

* cited by examiner

[FIG.1]
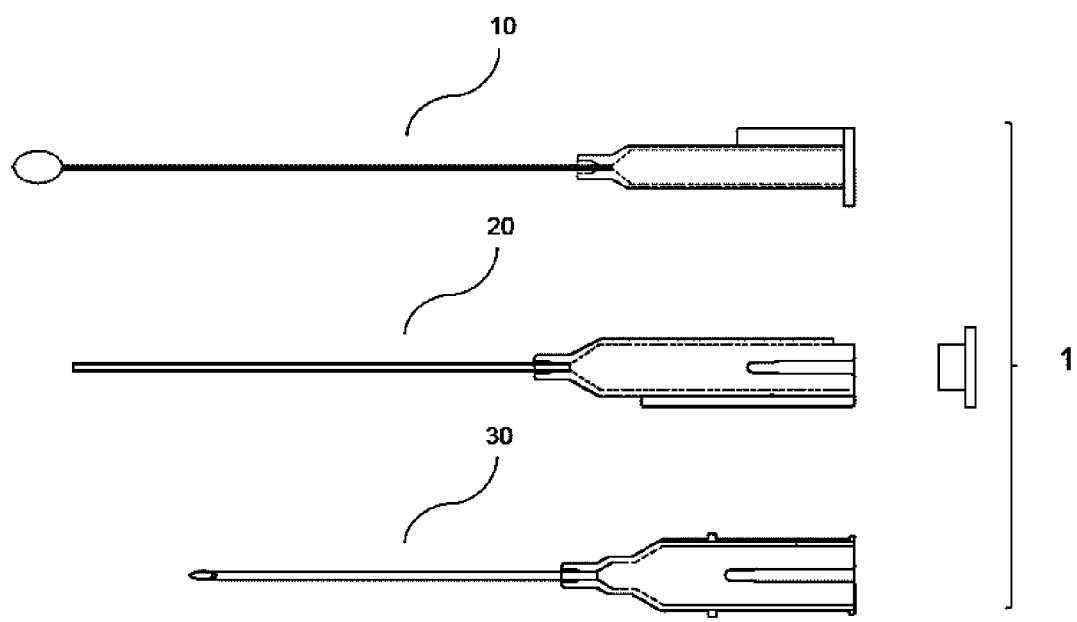

[FIG.2]
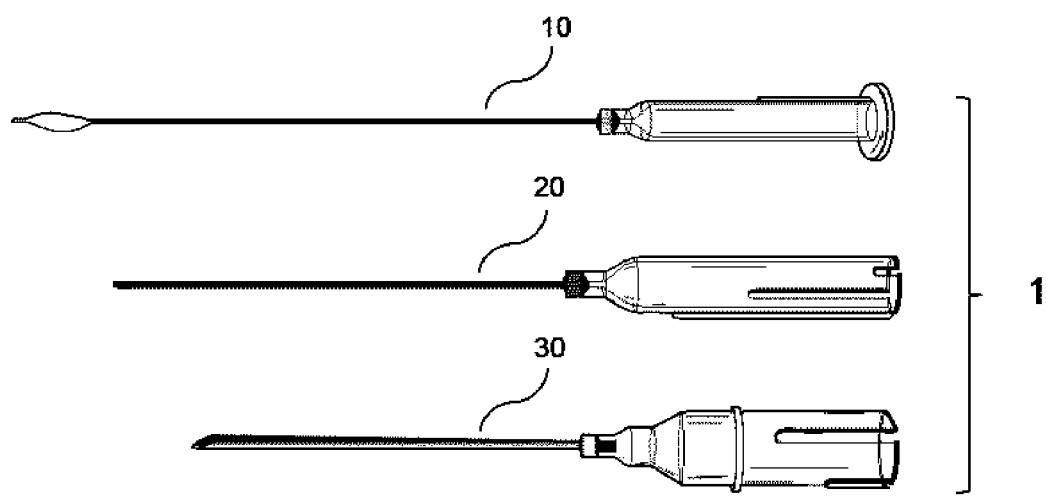

[FIG.3]
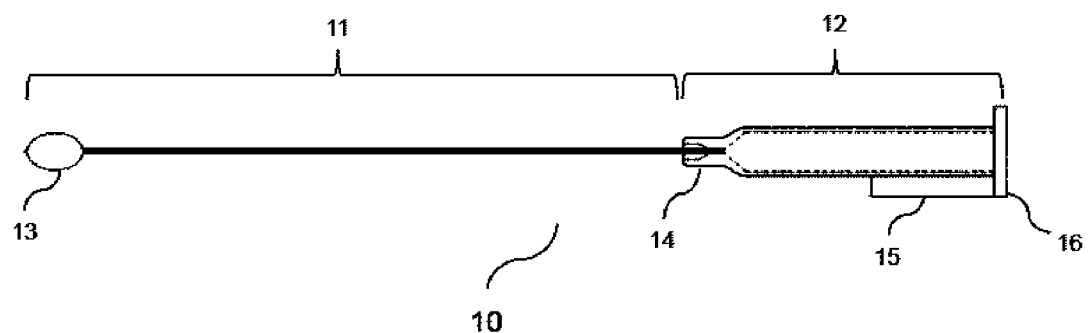

[FIG.4]
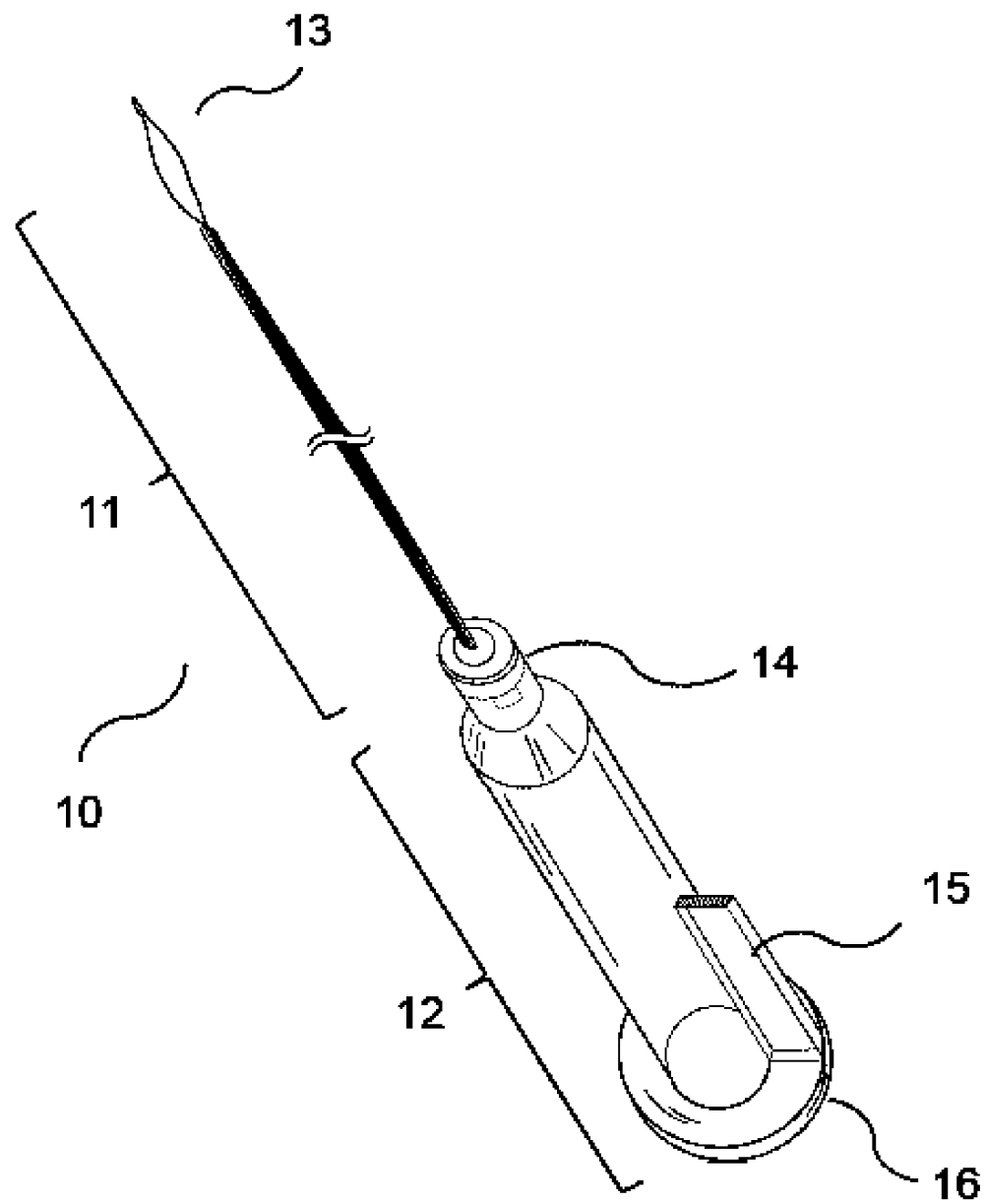

[FIG.5]
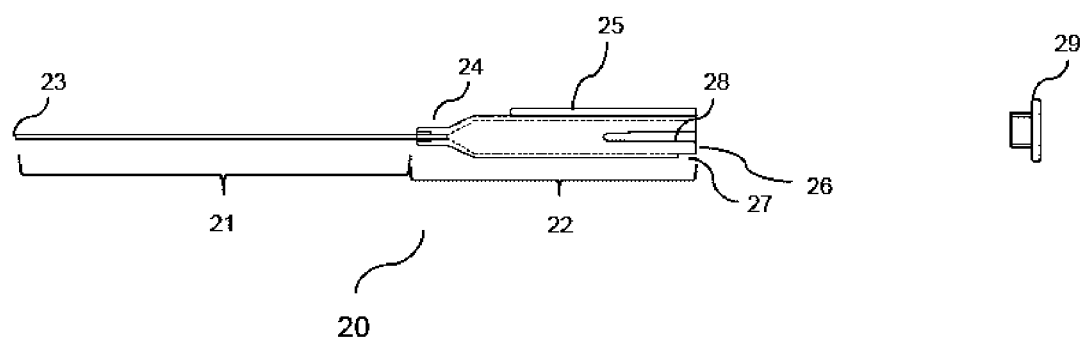

[FIG.6]
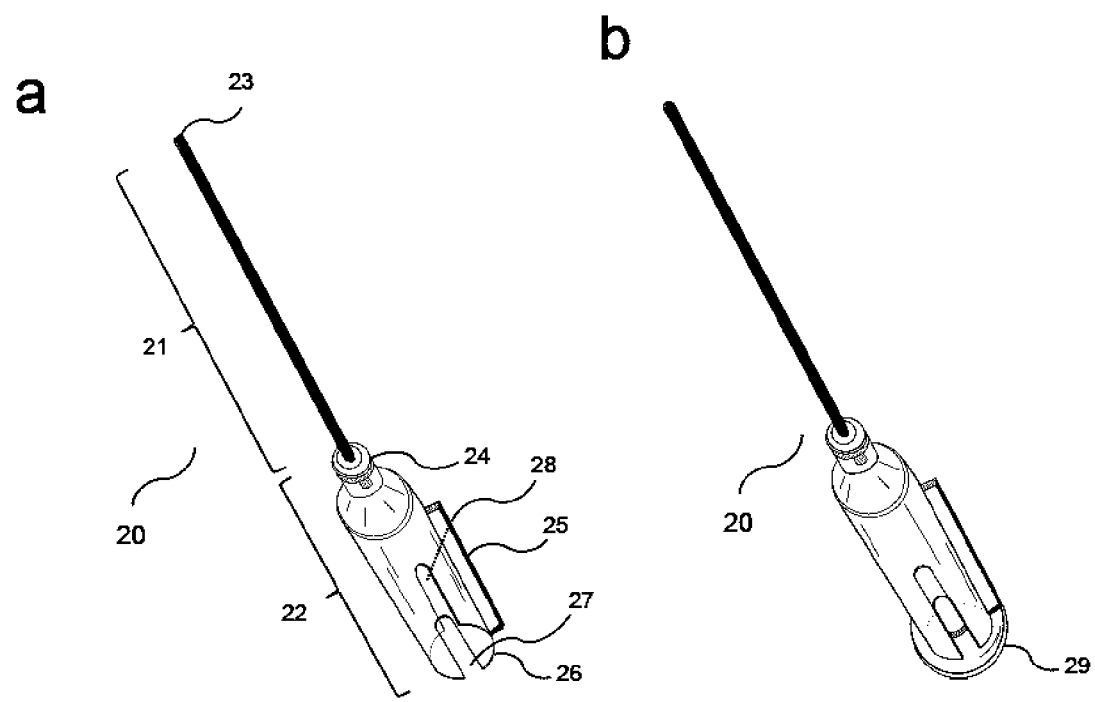

[FIG.7]
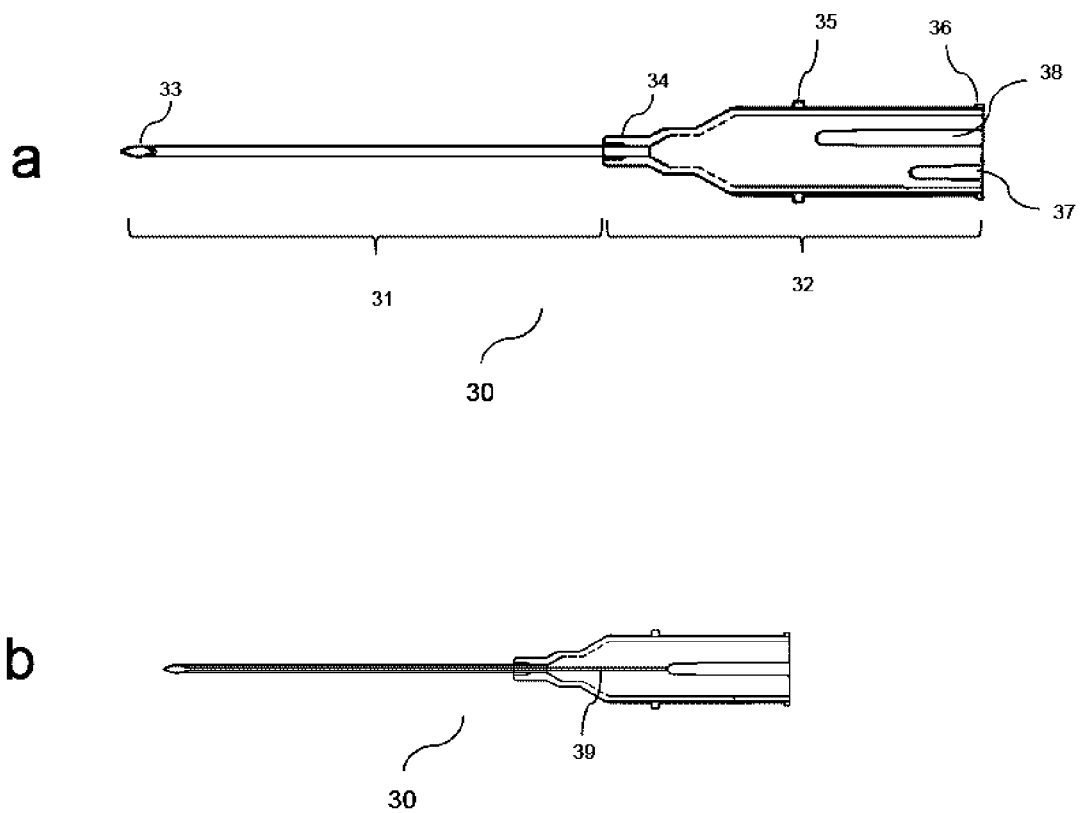

[FIG.8]
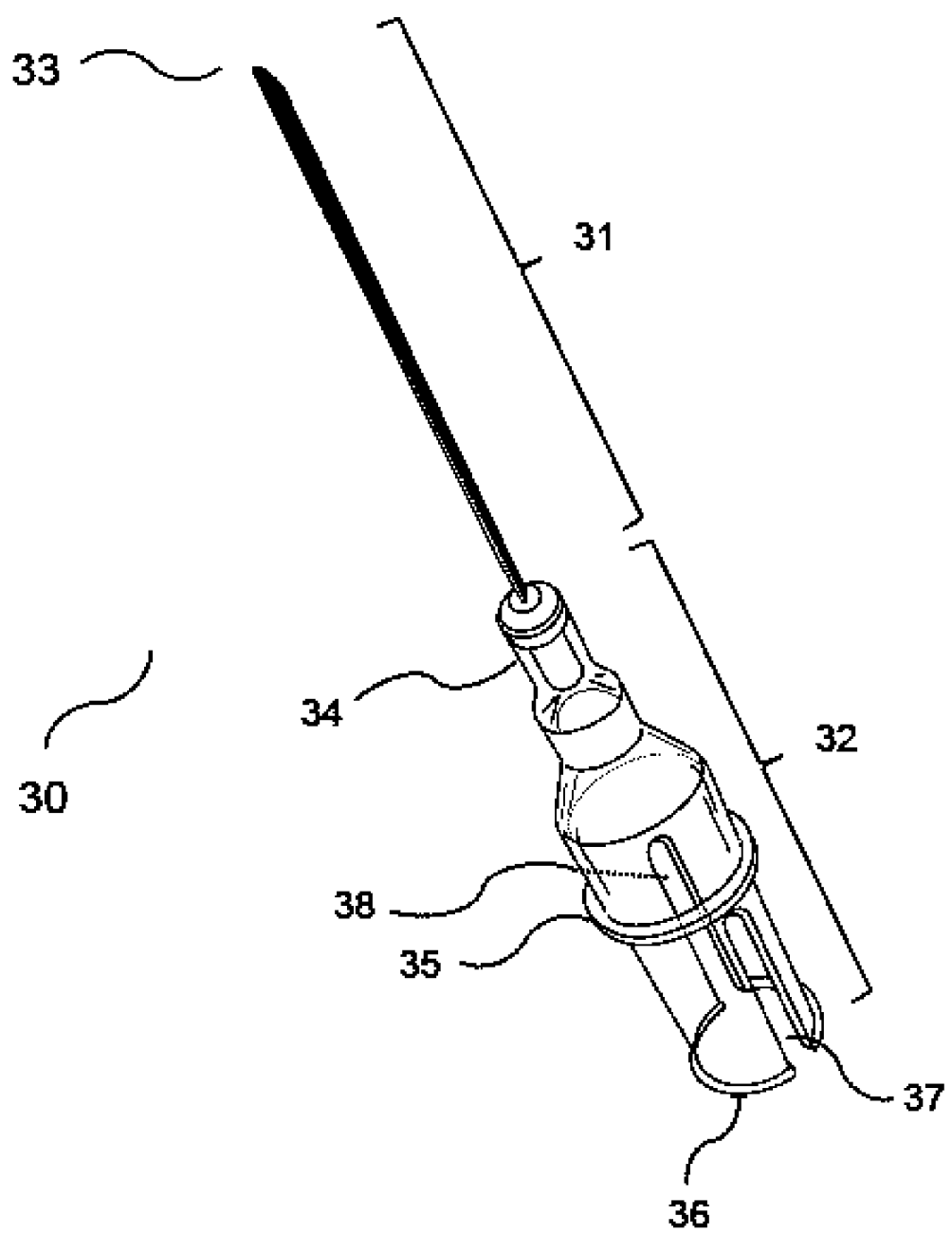

[FIG.9]
a
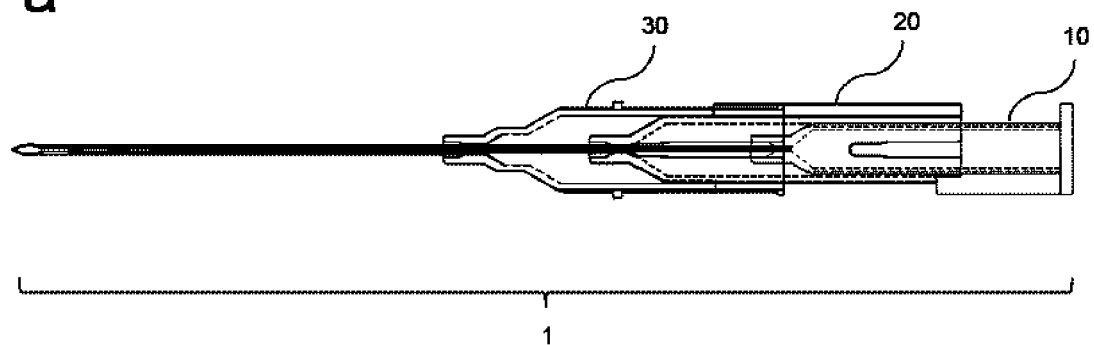
b
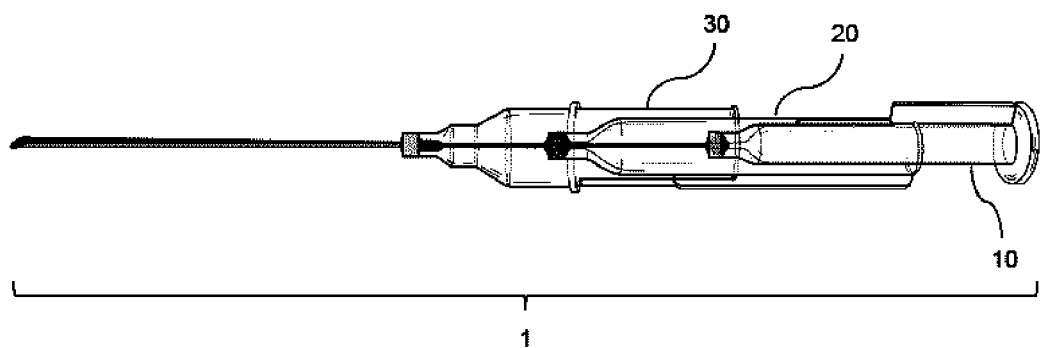

[FIG.10]
a
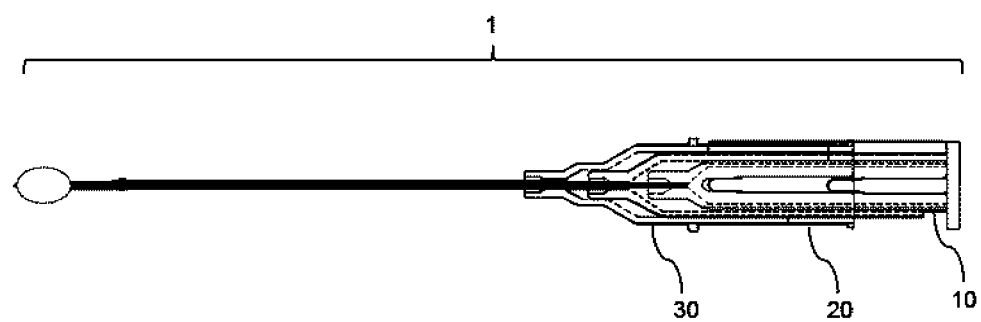
b
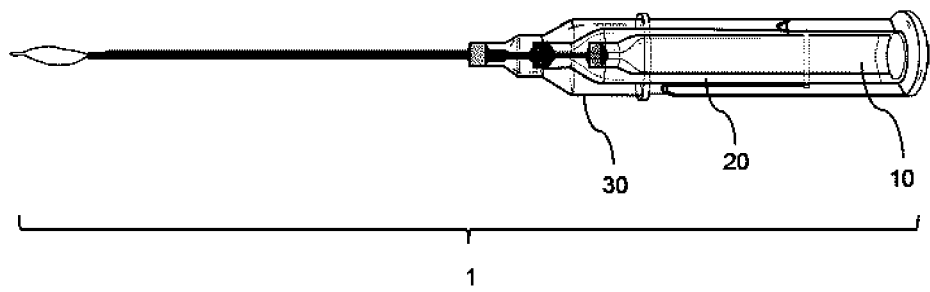

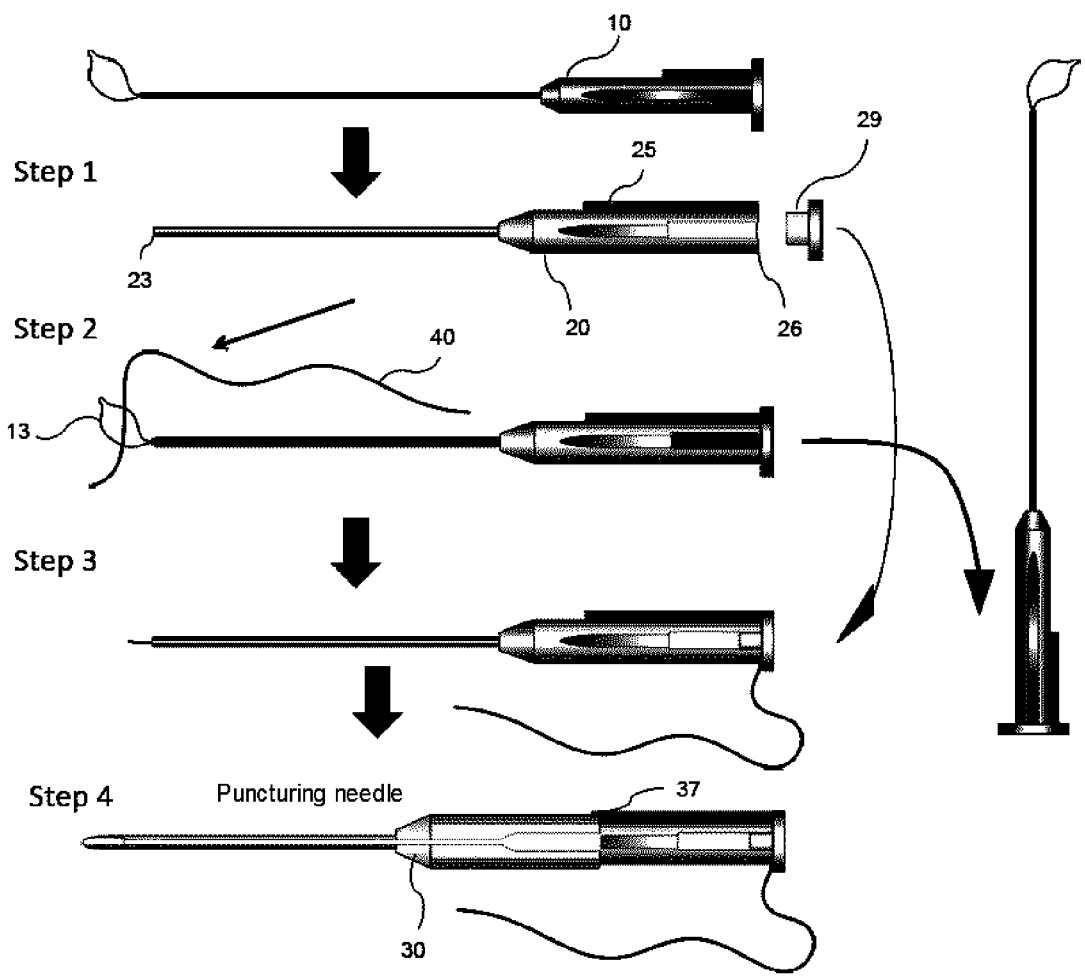

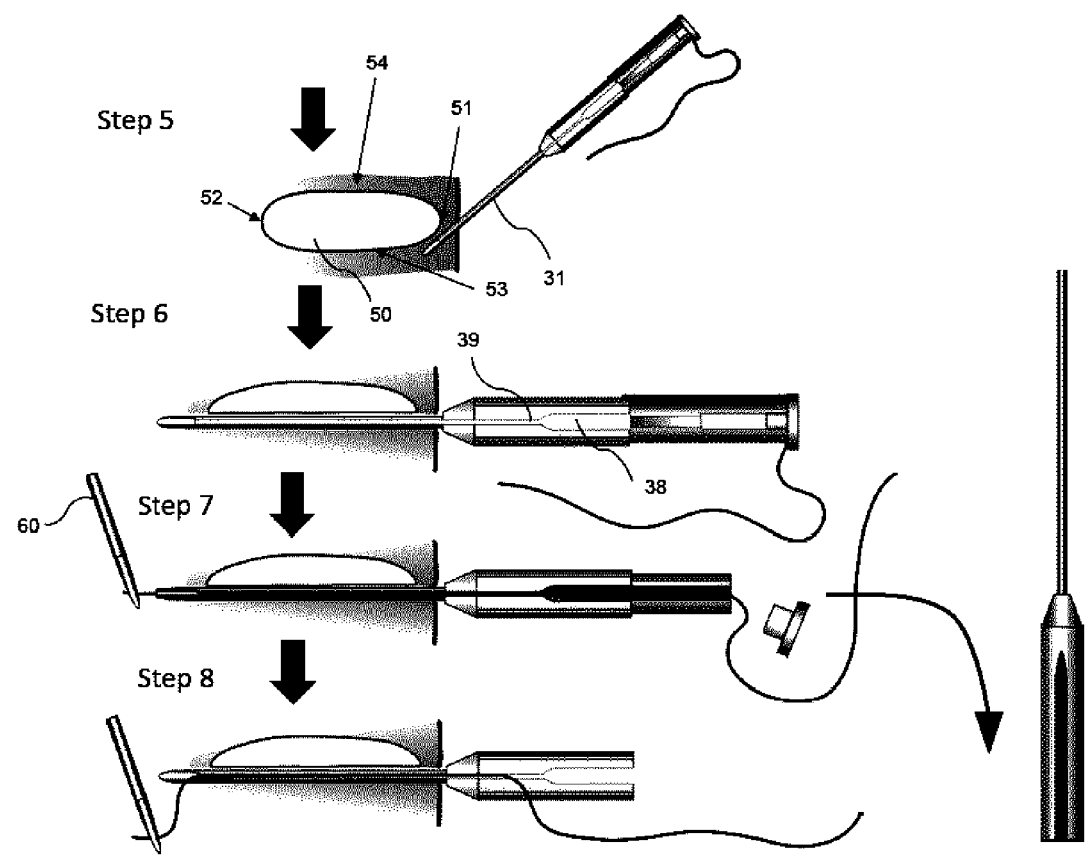
[FIG.12]

[FIG.13]
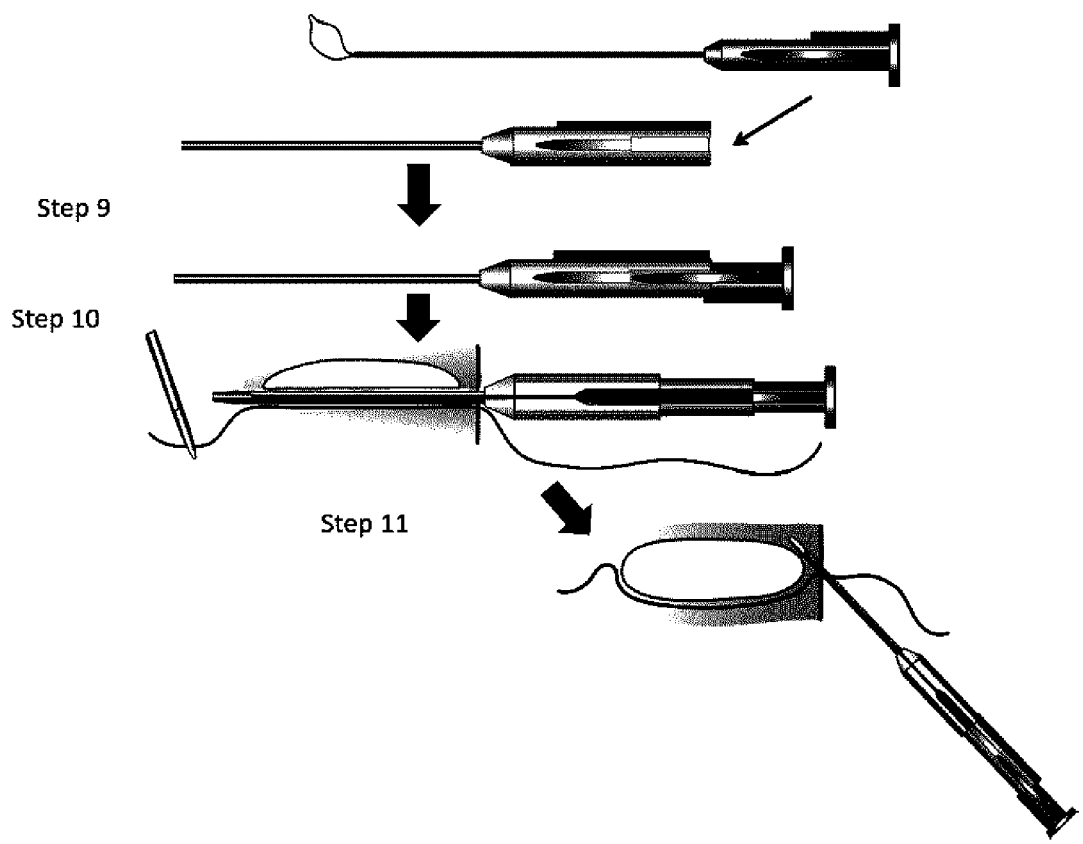
Step 9
Step 10
Step 11

[FIG.14]
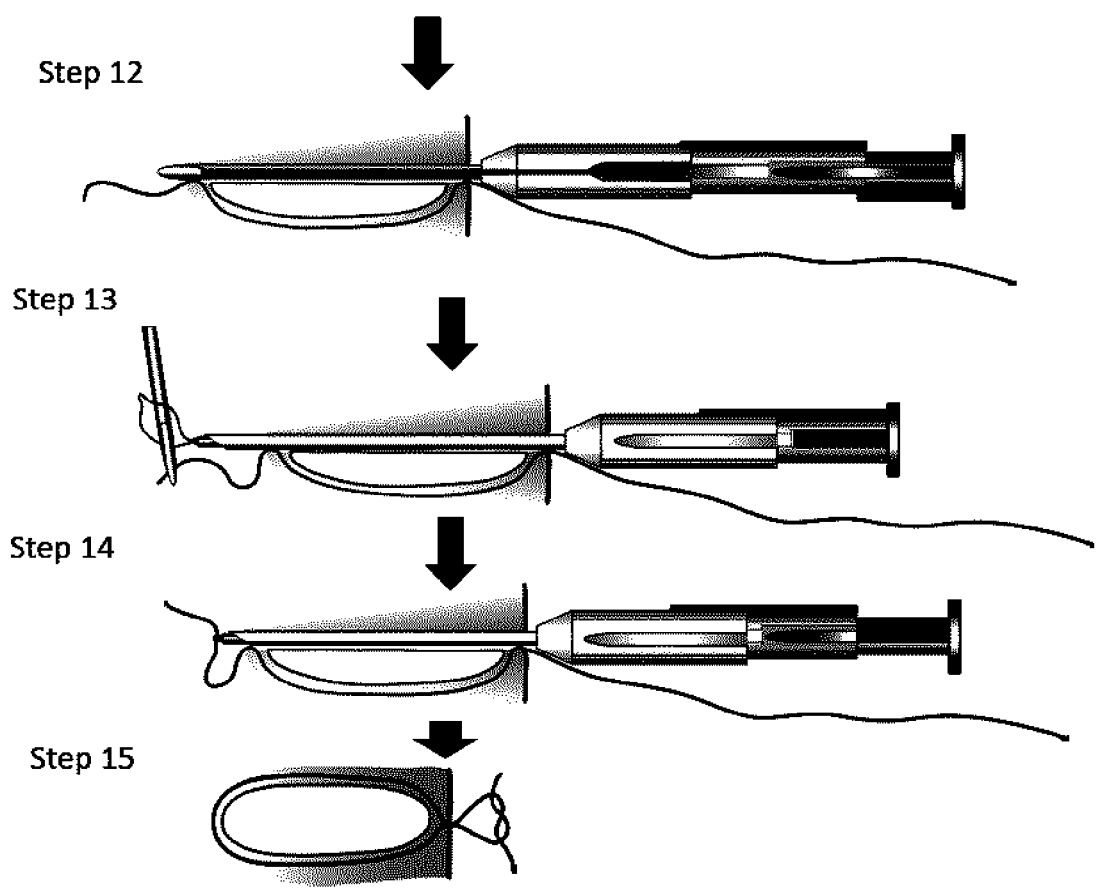

MEDICAL NEEDLE

CROSS-REFERENCE TO RELATED APPLICATION

The present application claims the benefit of priority to Japanese Patent Application No. 2014-184747, the disclosure of which is incorporated herein by reference in its entirety.

TECHNICAL FIELD

The present invention relates to medical needles for use in laparoscopic surgery.

BACKGROUND ART

Pediatric inguinal hernia is a congenital disease with about 20,000 cases reported in Japan each year, making it one of the most common diseases in pediatric surgery. In healthy boys, as the testes descend into the scrotum at birth, the peritoneum is drawn in along with the testes to form a sac within the scrotum. As the testes reach the scrotum, however, the sac formed by the peritoneum will be spontaneously closed. In the event that the sac-like peritoneum (i. e., hernia sac) is not closed and maintained, the intestine and other abdominal tissue may eventually enter the hernia sac. The condition is referred to as pediatric inguinal hernia. In girls, the round ligament of uterus extends from the upper lateral sides of uterus and follows the same path as the descending path of the testicles to hold the uterus in place. The ligament descends with a protrusion in the peritoneum, which, if not closed, forms a hernia sac.

The pediatric inguinal hernia is typically treated by surgical procedures involving ligation of the hernia sac at its neck (i.e., hernia orifice) using a suture. Two types of surgical procedures are used to treat pediatric inguinal hernia: open surgery and laparoscopic surgery. An open surgery is performed by incising the skin in the groin to pull out the hernia sac, and ligating the sac in the proximity of the hernia orifice. Involving incision in the groin, the open surgery tends to leave scars and cause significant post-surgical pain.

In contrast, a laparoscopic surgery, such as a technique known as laparoscopic percutaneous extraperitoneal closure (LPEC), is performed by inserting a laparoscope (i. e., camera) through a small opening formed in the umbilicus, and suture-ligating the vicinity of the hernia orifice using a surgical instrument while viewing the inside of the abdominal cavity on a monitor screen. As described, the LPEC technique is a less-invasive procedure that can eliminate the issues of scar formation and post-surgical pain associated with open surgery.

Known surgical instruments used in LPEC include a suture guide needle called Lapa-Her Closure™ as described in Non-Patent Document 1 (the entire disclosure of which is incorporated herein by reference) listed below.

PRIOR ART DOCUMENTS

Non-Patent Document

Non-Patent Document 1: Tamaki Iwade et al., The Shinshu Medical Journal, 61(3), pp. 139-147, 2013

DISCLOSURE OF THE INVENTION

Problems to Be Solved by the Invention

The suture guide needle as described in Non-Patent Document 1 can be used to percutaneously guide a suture along a hernia orifice. The suture guide needle in Non-Patent Document 1, however, has to puncture the affected site while the suture is attached to the needle tip. Even after puncturing, the manipulation of the guide needle from the upper rim of the hernia orifice along the lateral rim to the lower rim also needs to be performed with the suture being attached to the needle tip.

Thus, the LPEC procedure as described in Non-Patent Document 1 has been extremely difficult to perform since it requires the use of the needle with suture attached to its needle tip in the puncturing, manipulation and perforation steps during the percutaneous guidance of suture along the hernia orifice.

In view of the above-described problems, it is an objective of the present invention to provide a medical needle that makes easier the puncturing, manipulation and perforation steps during the percutaneous guidance of suture along the hernia orifice as compared to the suture guide needle described in Non-Patent Document 1 and thus can facilitate the LPEC procedure.

Means of Solving the Problems

In an effort to solve the above-described problems, the present inventors have succeeded in facilitating the puncturing, manipulation and perforation steps during the percutaneous guidance of suture along the hernia orifice by separately providing a puncturing member for puncturing and a loop member for capturing the suture. Surprisingly, the present inventors have succeeded in facilitating the grasping of suture at the distal end of the puncturing needle after the perforation step by further separately providing a threading member for threading the needle from inside and using the loop member, the threading member and the puncturing member, inserted one member into the next, in combination. Thus, the present inventors have succeeded in producing a medical needle that can facilitate the LPEC procedure. These successful examples ultimately led to the present invention.

According to the present invention, there is provided a medical needle, comprising a loop member including a loop needle with a loop-like distal end portion and a handle with an outer diameter larger than that of the loop needle; a threading member including a tubular threading needle and a tubular handle with an outer diameter larger than that of the threading needle, wherein the loop member can be inserted from a proximal end of the threading member; and a puncturing member including a tubular puncturing needle with a distal end portion having a sharp angle structure and a tubular handle with an outer diameter larger than that of the puncturing needle, wherein the threading member can be inserted from a proximal end of the puncturing member, wherein the medical needle is configured such that the length of the loop needle is greater than the length of the threading needle so that when the loop member is inserted into the threading member to the farthest point, the distal end portion of the loop needle protrudes from the distal end portion of the threading needle, and the length of the threading needle is greater than the length of the puncturing needle so that when the threading member is inserted into the puncturing member to the farthest point, the distal end portion of the threading needle protrudes from the distal end portion of the puncturing needle. Preferably, the threading member includes a tubular threading needle and a tubular handle with an outer diameter larger than that of the threading needle, wherein the loop member can be inserted from the proximal end of the threading member, wherein the threading member has a distal end portion that has a non-loop-like structure.

In the medical needle of the present invention, preferably, a radial projection is provided on the handle of the loop member and first and second cutouts are provided in the handle of the threading member that each extend longitudinally from the proximal end, such that the projection of the loop member can engage with the first and second cutouts of the threading member. The depth of the first cutout of the threading member is such that when the projection of the loop member engages with the first cutout of the threading member, the distal end portion of the loop needle does not protrude from the distal end portion of the threading needle. The depth of the second cutout of the threading member is such that when the projection of the loop member engages with the second cutout of the threading member, the distal end portion of the loop needle protrudes from the distal end portion of the threading needle.

In the medical needle of the present invention, preferably, a radial projection is provided on the handle of the threading member and first and second cutouts are provided in the handle of the puncturing member that each extend longitudinally from the proximal end, such that the projection of the threading member can engage with the first and second cutouts of the puncturing member. The depth of the first cutout of the puncturing member is such that when the projection of the threading member engages with the first cutout of the puncturing member, the distal end portion of the threading needle does not protrude from the distal end portion of the puncturing needle. The depth of the second cutout of the puncturing member is such that when the projection of the threading member engages with the second cutout of the puncturing member, the distal end portion of the threading needle protrudes from the distal end portion of the puncturing needle.

In the medical needle of the present invention, the threading member preferably includes an attachment that can be removably fitted to the proximal end of the threading member.

In the medical needle of the present invention, a third cutout is preferably provided in the puncturing member that is larger than the diameter of the suture and extends longitudinally from the distal end portion of the puncturing needle to the proximal end of the handle of the puncturing member.

Preferably, the medical needle of the present invention is a needle for treating pediatric inguinal hernia.

Advantageous Effects of Invention

The medical needle of the present invention employs so called a three-stage rocket format. In other words, the diameters of the needles and handles (or grips) of the loop member, the threading member and the puncturing member that compose the medical needle of the present invention may be varied such that the threading member and the loop member can be successively nested in the puncturing member to form a single unit that can be used for puncturing and retrieving of the suture.

In comparison to the suture guide needle described in Non-Patent Document 1, the medical needle of the present invention makes it possible to easily guide a suture percutaneously along a hernia orifice and thus facilitates the LPEC procedure since it can achieve puncturing, manipulation and perforation steps by using a puncturing member with a threading member inserted therethrough and with the suture not extending from the tip of the puncturing needle. Further, the puncturing member can serve as an outer casing that an operator can hold to handle the needle. This facilitates the puncturing. Accordingly, the LPEC procedure when performed using the medical needle of the present invention can save time as compared to the conventional LPEC procedure and is thus expected to reduce the burden for both the operators and the patients.

BRIEF DESCRIPTION OF DRAWINGS

FIG. 1 is a cross-sectional plan view of one embodiment of a medical needle of the present invention.

FIG. 2 is an external view of one embodiment of the medical needle of the present invention.

FIG. 3 is a cross-sectional plan view of a loop member according to one embodiment of the medical needle of the present invention.

FIG. 4 is a perspective view of the loop member according to one embodiment of the medical needle of the present invention.

FIG. 5 is a cross-sectional plan view of a threading member according to one embodiment of the medical needle of the present invention.

FIG. 6 is a perspective view of the threading member according to one embodiment of the medical needle of the present invention, in which (a) is a perspective view of the threading member with its proximal end open and (b) is a perspective view of the threading member with its proximal end closed with an attachment 29 fitted thereto.

FIG. 7 is a cross-sectional plan view of a puncturing member according to one embodiment of the medical needle of the present invention, in which (a) is a cross-sectional plan view of the puncturing member without a puncturing member entire cutout 39 and (b) is a cross-sectional plan view of the puncturing member with the puncturing member entire cutout 39.

FIG. 8 is a perspective view of the puncturing member according to one embodiment of the medical needle of the present invention.

FIG. 9 shows (a) a cross-sectional plan view and (b) an external view of one embodiment of the medical needle of the present invention.

FIG. 10 shows (a) a cross-sectional plan view and (b) an external view of one embodiment of the medical needle of the present invention.

FIG. 11 is a schematic diagram illustrating a method of using one embodiment of the medical needle of the present invention.

FIG. 12 is a schematic diagram illustrating a method of using one embodiment of the medical needle of the present invention.

FIG. 13 is a schematic diagram illustrating a method of using one embodiment of the medical needle of the present invention.

FIG. 14 is a schematic diagram illustrating a method of using one embodiment of the medical needle of the present invention.

DESCRIPTION OF EMBODIMENTS

While a medical needle 1 according to one embodiment of the present invention comprising a loop member 10, a threading member 20, and a puncturing member 30 will specifically be described in the following with reference to FIGS. 1 to 10, it is to be understood that the present invention is not limited to what is embodied in these drawings.

As depicted in FIGS. 1 and 2, the medical needle 1 consists of the loop member 10, the threading member 20, and the puncturing member 30. The loop member 10, the threading member 20, and the puncturing member 30 are shown in FIG. 3 through FIG. 8 in respective cross-sectional views and perspective views. These members will now be described with reference to FIGS. 3, 5, and 7, each by way of a cross-sectional view.

The loop member 10 includes a loop needle 11 and a loop handle 12. The loop needle 11 has a loop structure at its distal end portion 13. The size of the loop is not particularly limited as long as a suture can be inserted therethrough. The body of the loop needle 11 may or may not have a hollow tubular structure. The loop needle 11 and the loop handle 12 are connected and held together via a loop needle joint 14 (i.e., needle hub). The loop handle 12 has a cylindrical structure having a larger outer diameter than that of the loop needle 11. The loop handle 12 may or may not have a tubular structure. The loop handle 12 has a loop handle proximal end portion 16 that is opposite the loop needle joint 14 connected to the loop needle 11. The loop handle proximal end portion 16 preferably has a disc structure having a cross-section larger than the inner diameter of a threading handle 22 described below.

The threading member 20 includes a threading needle 21 and a threading handle 22. The threading needle 21 has a hollow tubular structure. The distal end portion 23 of the threading needle 21 is not particularly limited and may have any structure such as a right angle and a sharp angle. The threading needle 21 and the threading handle 22 are connected and held together via a threading needle joint 24 (i.e., needle hub). The threading handle 22 has a circular tube structure having a larger outer diameter than that of the threading needle 21. The threading handle 22 has a threading handle proximal end portion 26 that is opposite the threading needle joint 24 connected to the threading needle 21 and through which the loop member 10 can be inserted. Thus, the inner diameter of the threading needle 21 is larger than the outer diameter of the loop needle 11 and the inner diameter of the threading handle 22 is larger than the outer diameter of the loop handle 12. The threading handle proximal end portion 26 may be an open end or alternatively, may have a removable attachment 29 fitted in the open end.

The puncturing member 30 includes a puncturing needle 31 and a puncturing handle 32. The puncturing needle 31 has a hollow tubular structure. The distal end portion 33 of the puncturing needle 31 is not particularly limited as long as it has a sufficiently sharp angle structure to puncture the skin of the subject. The puncturing needle 31 and the puncturing handle 32 are connected and held together via a puncturing needle joint 34 (i.e., needle hub). The puncturing handle 32 has a circular tube structure having a larger outer diameter than that of the puncturing needle 31. The puncturing handle 32 has a puncturing handle proximal end portion 36 that is opposite the puncturing needle joint 34 connected to the puncturing needle 31 and through which the threading member 20 can be inserted. Thus, the inner diameter of the puncturing needle 31 is larger than the outer diameter of the threading needle 21 and the inner diameter of the puncturing handle 32 is larger than the outer diameter of the threading handle 22.

The loop needle 11, the threading needle 21 and the puncturing needle 31 have decreasing lengths in this order. In other words, the loop needle 11 is formed to have a greater length than the threading needle 21. Specifically, the loop needle 11 is formed to have a greater length than the threading needle 21 such that when the loop member 10 is inserted into the threading member 20 to the farthest point, the distal end portion 13 of the loop needle 11 extends from the distal end portion 23 of the threading needle 21. The threading needle 21 is formed to have a greater length than the puncturing needle 31. Specifically, the threading needle 21 is formed to have a greater length than the puncturing needle 31 such that when the threading member 20 is inserted into the puncturing member 30 to the farthest point, the distal end portion of the threading needle 21 extends from the distal end portion 33 of the puncturing needle 31. While the length of the puncturing needle 31 is not particularly limited, the length needs to be greater than the expected maximum diameter of the hernia orifice. The term "needle length" as used herein refers to the entire length of a needle extending from its distal end portion to its needle joint.

While the medical needle of the present invention may take any form as long as it includes a loop member, a threading member and a puncturing member having respective structures as described above, it may include projections and cutouts as shown in FIGS. 1 to 10.

Accordingly, the loop handle 12 has a loop handle projection 15 that projects in the direction of height, or radially, and extends distally from the loop handle proximal end portion 16. The threading handle 22 has first and second cutouts, in particular a threading handle short cutout 27 and a threading handle long cutout 28, that each extend distally from the threading handle proximal end portion 26. The loop handle projection 15 can engage with each of the threading handle short cutout 27 and the threading handle long cutout 28. Specifically, the radial depth of each of the threading handle short cutout 27 and the threading handle long cutout 28 is greater than the height of the loop handle projection 15. The depth (i.e., width) of the threading handle short cutout 27 is such that the distal end portion 13 of the loop needle 11 does not extend from the distal end portion 23 of the threading needle 21 when the loop handle projection 15 is engaged with the threading handle short cutout 27. The depth of the threading handle long cutout 28 is such that the distal end portion 13 of the loop needle 11 extends from the distal end portion 23 of the threading needle 21 when the loop handle projection 15 is engaged with the threading handle long cutout 28.

Similar to the loop handle projection 15, the threading handle 22 has a threading handle projection 25 that projects radially and extends distally from the threading handle proximal end portion 26. The puncturing handle 32 has first and second cutouts, in particular a puncturing handle short cutout 37 and a puncturing handle long cutout 38, that each extend distally from the puncturing handle proximal end portion 36. The threading handle projection 25 can engage with each of the puncturing handle short cutout 37 and the puncturing handle long cutout 38. Specifically, the radial depth of each of the puncturing handle short cutout 37 and the puncturing handle long cutout 38 is greater than the height of the threading handle projection 25. The depth (i.e., width) of the puncturing handle short cutout 37 is such that the distal end portion 23 of the threading needle 21 does not extend from the distal end portion 33 of the puncturing needle 31 when the threading handle projection 25 is engaged with the puncturing handle short cutout 37. The depth of the puncturing handle long cutout 38 is such that the distal end portion 23 of the threading needle 21 extends from the distal end portion 33 of the puncturing needle 31 when the threading handle projection 25 is engaged with the puncturing handle long cutout 38.

In addition to the puncturing handle short cutout 37 and the puncturing handle long cutout 38, the puncturing member preferably has a third cutout, in particular a puncturing member entire cutout 39, that is larger than the suture diameter and extends longitudinally from the puncturing needle distal end portion 33 to the puncturing handle proximal end portion 36. In other words, the puncturing member entire cutout 39 is a cutout provided over the entire length of the puncturing member. As shown in FIG. 13, since the puncturing member 30 has the puncturing member entire cutout 39, the suture 40 can be displaced out of the puncturing member 30 from the puncturing member entire cutout 39 by inserting the threading member 20 into the puncturing member 30 with the suture 40 remaining within the lumen of the puncturing member 30. Thus, when the puncturing needle 31 is punctured into the body of the subject, the suture 40 within the puncturing member 30 can be placed and left within the body of the subject without removing the puncturing needle 31 from the body. This significantly facilitates the subsequent procedures and is thus advantageous.

FIGS. 9 and 10 each show a cross-sectional plan view and an external view of the loop member 10, the threading member 20 and the puncturing member 30, inserted one member into the next, to form a single unit. In FIG. 9, the loop handle projection 15 is engaged with the threading handle short cutout 27 and the threading handle projection 25 is engaged with the puncturing handle short cutout 37. In this configuration, neither the loop needle distal end portion 13 nor the threading needle distal end portion 23 extends out from the puncturing needle distal end portion 33. In FIG. 10, the loop handle projection 15 is engaged with the threading handle long cutout 28 and the threading handle projection 25 is engaged with the puncturing handle long cutout 38. In this configuration, the loop needle distal end portion 13 and the threading needle distal end portion 23 extend from the puncturing needle distal end portion 33.

The medical needle of the present invention is not particularly limited as long as it has the above-described structure and various modifications can be made to the extent that the objectives of the present invention are achieved. For example, surface features may be provided on the surface of the handles of the loop member, the threading member and the puncturing member in order to provide a better grip when holding the medical needle of the present invention. Also, as shown in FIG. 7, a circumferential puncturing finger stop 35 is preferably provided on the handle 32 of the puncturing member 30, which serves as an outer casing when the members are assembled into a single unit, in order to facilitate engagement with fingers.

The medical needle of the present invention can be used in surgical procedures to treat, for example, pediatric inguinal hernia. As described, a preferred embodiment of the medical needle of the present invention is a needle for treating pediatric inguinal hernia. It should be noted, however, that the medical needle of the present invention can be applicable to laparoscopic surgery not only in children, but also in adult patients, as it can serve to allow a surgeon to introduce suture into the abdominal cavity, form a loop within the abdominal cavity, and then draw the other end of the suture out of the abdominal cavity, without leaving scars, as well as to allow him to manipulate the needle from outside of the abdominal cavity to pass the suture through an internal organ to ligate it. Other examples of surgical procedures to which the medical needle of the present invention is applicable include ligature resection in the testicular vein ligation for testicular vein varicosis, retention of the testicular artery and vein and ductus deference in the abdominal cavity during orchiopexy, retention of the intestine during appendectomy, retention of the colon during colectomy, retention of the gall bladder during cholecystectomy, retention of the ureter during hydronephrosis and hydroureter surgery, suture closure of the absent diaphragm in diaphragmatic hernia, gastric fundplication in esophageal hiatal hernia, fixation of the anterior wall of stomach in stomach volvulus, laparoscopic gastrostomy, and resection of Meckel diverticulum. Steps of using one embodiment of the medical needle of the present invention in pediatric inguinal hernia surgery will now be described with reference to FIGS. 11 to 14.

First, the attachment 29 fitted to the threading handle proximal end portion 26 of the threading member 20 is removed and the loop member 10 is inserted into the threading member 20 to the farthest point (Step 1 in FIG. 11). Next, once the loop needle distal end portion 13 protrudes from the threading needle distal end portion 23, suture 40 is passed through the loop needle distal end portion 13 (Step 2 in FIG. 11). In this state, the loop member 10 is pulled out from the threading member 20 to pull the suture 40 through the lumen of the threading member 20. With about one centimeter of one end of the suture protruding from the threading needle distal end portion 23 and the other end of the suture coming out from the threading handle proximal end portion 26, the attachment 29 is fitted to the threading handle proximal end portion 26 to secure the suture 40 (Step 3 in FIG. 11). The threading member 20 with the suture 40 extending therethrough is then inserted into the puncturing member 30. Specifically, the threading handle projection 25 is engaged with the puncturing handle short cutout 37 such that the threading needle distal end portion 23 and the suture 40 do not protrude from the puncturing needle distal end portion 33. In this state, the puncturing member 30 and the threading member 20 are secured to one another as a single unit (Step 4 in FIG. 11).

Next, the puncturing needle 31 is punctured through the skin of the subject (Step 5 in FIG. 12), then advanced through the subcutaneous tissue and muscles. Specifically, the puncturing needle 31 is manipulated in the extraperitoneal space from the hernia orifice upper rim 51 along the hernia orifice lateral rim 53 toward the hernia orifice lower rim 52 where it is advanced to perforate into the abdominal cavity (Step 6 in FIG. 12). Next, the threading handle projection 25 is disengaged from the puncturing handle short cutout 37 and the threading member 20 is moved circumferentially within the puncturing member 30 until the threading handle projection 25 engages with the puncturing handle long cutout 38. This engagement causes the threading needle distal end portion 23 and the suture 40 to protrude from the puncturing needle distal end portion 33. In this state, the puncturing member 30 and the threading member 20 are secured to one another as a single unit. The part of the suture 40 protruding from the threading needle distal end portion 23 is then grasped by a grasper 60 and the attachment 29 fitted to the threading handle proximal end portion 26 is removed (Step 7 in FIG. 12). Next, the threading member 20 is removed from the puncturing member 30, leaving the suture 40 within the lumen of the puncturing member 30 with one end of the suture 40 extending from the hernia orifice lower rim 52 (Step 8 in FIG. 12).

Next, the loop member 10 is inserted into the threading member 20 so that the loop handle projection 15 engages with the threading handle short cutout 27 to secure the loop member 10 to the threading member 20 (Step 9 in FIG. 13). Subsequently, the threading member 20 with the loop member 10 inserted therethrough is inserted into the puncturing member 30 so that the threading handle projection 25 engages with the puncturing handle short cutout 37 to secure the threading member 20 to the puncturing member 30 (Step 10 in FIG. 12). Upon this, neither the threading needle distal end portion 23 nor the loop needle distal end portion 13 extends out from the puncturing needle distal end portion 33. When the puncturing member entire cutout 39 is provided on the puncturing member 30, the suture 40 residing within the lumen of the puncturing member 30 can be fully displaced through the puncturing member entire cutout 39 into the extraperitoneal space of the subject. Then, the puncturing needle 31 is retracted, leaving the suture 40 within the extraperitoneal space of the subject (Step 11 in FIG. 13).

When the puncturing member entire cutout 39 is not provided on the puncturing member 30, the puncturing member 30 after Step 8 in FIG. 12 is removed from the abdominal cavity so that one end of the suture 40 extends from the hernia orifice lower rim 52 with the rest of the suture 40 remaining within the abdominal cavity along the hernia orifice lateral rim 53 and the other end of the suture 40 extending from the hernia orifice upper rim 51. Next, the loop member 10 is inserted into the threading member 20 so that the loop handle projection 15 engages with the threading handle short cutout 27 to secure the loop member 10 to the threading member 20 and then the threading member 20 with the loop member 10 inserted therethrough is inserted into the puncturing member 30 so that threading handle projection 25 engages with the puncturing handle short cutout 37 to secure the threading member 20 to the puncturing member 30. Upon this, neither the threading needle distal end portion 23 nor the loop needle distal end portion 13 extends out from the puncturing needle distal end portion 33. With the needle assembly held in this state, the puncturing needle 31 is punctured through the skin of the subject from the same perforation site as in the above-described Step 5 to reach the state after the above-described Step 11 is implemented.

Next, the puncturing needle 31 is advanced through the subcutaneous tissue and muscles. Specifically, the puncturing needle 31 is manipulated in the extraperitoneal space from the hernia orifice upper rim 51 along the hernia orifice medial rim 54 toward the hernia orifice lower rim 52 where it is advanced to perforate again into the abdominal cavity from the original perforation site (Step 12 in FIG. 14). Next, the threading handle projection 25 is disengaged from the puncturing handle short cutout 37 and the threading member 20 is moved circumferentially within the puncturing member 30 until the threading handle projection 25 engages with the puncturing handle long cutout 38. Similarly, the loop handle projection 15 is disengaged from the threading handle short cutout 27 and the loop member 10 is moved circumferentially within the threading member 20 until the loop handle projection 25 engages with the threading handle long cutout 28. These engagements cause the threading needle distal end portion 23 and the loop needle distal end portion 13 to protrude from the puncturing needle distal end portion 33. In this state, the puncturing member 30, the threading member 20 and the loop member 10 are secured to one another as a single unit. Next, using the grasper 60, the end of the suture 40 extending from the hernia orifice lower rim 52 is guided through the loop needle distal end portion 13 (Step 13 in FIG. 14).

Next, the threading handle projection 25 is disengaged from the puncturing handle long cutout 38 and the threading member 20 is moved circumferentially within the puncturing member 30 until the threading handle projection 25 engages with the puncturing handle short cutout 37. Similarly, the loop handle projection 15 is disengaged from the threading handle long cutout 28 and the loop member 10 is moved circumferentially within the threading member 20 until the loop handle projection 15 engages with the threading handle short cutout 27. These engagements secure the suture 40 guided through the loop needle distal end portion 13 (Step 14 in FIG. 14). With the needle assembly held in this state, the puncturing needle 31 is removed such that the both ends of the suture 40 extend from the hernia orifice upper rim 51. Next, the ends of the suture 40 are tied together to ligate the hernia orifice 50 (Step 15 in FIG. 14). The ligature of the suture 40 is embedded subcutaneously.

REFERENCE SIGNS LIST

1: medical needle
10: loop member
11: loop needle
12: loop handle
13: loop needle distal end portion
14: loop needle joint
15: loop handle projection
16: loop handle proximal end portion
20: threading member
21: threading needle
22: threading handle
23: threading needle distal end portion
24: threading needle joint
25: threading handle projection
26: threading handle proximal end portion
27: threading handle short cutout
28: threading handle long cutout
29: attachment
30: puncturing member
31: puncturing needle
32: puncturing handle
33: puncturing needle distal end portion
34: puncturing needle joint
35: puncturing finger stop
36: puncturing handle proximal end portion
37: puncturing handle short cutout
38: puncturing handle long cutout
39: puncturing member entire cutout
40: suture
50: hernia orifice
51: hernia orifice upper rim
52: hernia orifice lower rim
53: hernia orifice lateral rim
54: hernia orifice medial rim
60: grasper

The invention claimed is:

1. A medical needle tool, comprising a suture and a medical needle, wherein the medical needle comprises a loop member, a threading member and a puncturing member, wherein the loop member is insertable into the threading member and the threading member is insertable into the puncturing member;

the loop member including a loop needle having a body portion that has a loop shaped distal end portion, the loop member further including a handle having an outer diameter larger than that of the loop needle in a direction perpendicular to a longitudinal direction of the loop needle, a proximal end of the bop needle being connected to the handle;

the threading member including a tubular threading needle and a tubular handle, the tubular handle having an outer diameter larger than that of the threading needle, wherein the loop member can be inserted from a proximal end of the threading member, wherein the threading member has a distal end portion that has a non-loop-like structure; and the puncturing member including a tubular puncturing needle that has a distal end portion having a sharp angle structure, the puncturing member having a proximal end having a tubular handle with an outer diameter larger than that of the puncturing needle, wherein the threading member can be inserted from the proximal end of the puncturing member, wherein the medical needle is configured such that a length of the loop needle is greater than a length of the threading needle so that when the loop member is inserted into the threading member to a farthest point, the distal end portion of the loop needle protrudes from the distal end portion of the threading member, and the length of the threading needle is greater than a length of the puncturing needle so that when the threading member is inserted into the puncturing member to a farthest point, the distal end portion of the threading member protrudes from the distal end portion of the puncturing needle, wherein the medical needle tool is a tool for treating pediatric inguinal hernia, wherein the body portion of the loop needle has a hollow tubular structure, and wherein the suture is passed through the distal end portion of the loop needle.

2. The medical needle tool of claim 1, wherein a radial projection is provided on the handle of the loop member, first and second cutouts are provided in the tubular handle of the threading member such that each extend longitudinally from the proximal end of the threading member, such that the radial projection of the loop member can engage with the first and second cutouts of the threading member, a depth of the first cutout of the threading member is such that when the radial projection of the loop member engages with the first cutout of the threading member, the distal end portion of the loop needle does not protrude from the distal end portion of the threading member, and a depth of the second cutout of the threading member is such that when the radial projection of the loop member engages with the second cutout of the threading member, the distal end portion of the loop needle protrudes from the distal end portion of the threading member.

3. The medical needle tool of claim 1, wherein a radial projection is provided on the tubular handle of the threading member, first and second cutouts are provided in the tubular handle of the puncturing member such that each extend longitudinally from the proximal end of the puncturing member, such that the radial projection of the threading member can engage with the first and second cutouts of the puncturing member, a depth of the first cutout of the puncturing member is such that when the radial projection of the threading member engages with the first cutout of the puncturing member, the distal end portion of the threading member does not protrude from the distal end portion of the puncturing needle, and a depth of the second cutout of the puncturing member is such that when the radial projection of the threading member engages with the second cutout of the puncturing member, the distal end portion of the threading member protrudes from the distal end portion of the puncturing needle.

4. The medical needle tool of claim 1, wherein the threading member includes an attachment that can be removably fitted to the proximal end of the threading member.

5. The medical needle tool of claim 3, wherein a third cutout is provided in the puncturing member that is larger than a diameter of the suture and extends longitudinally from the distal end portion of the puncturing needle to the tubular handle of the puncturing member.

\* \* \* \* \*